(12) United States Patent
Winter et al.

(10) Patent No.: US 12,303,102 B2
(45) Date of Patent: May 20, 2025

(54) CLAMPING DEVICE FOR ACTING ONTO A MEDICAL TUBING

(71) Applicant: Fresenius Kabi Deutschland GmbH, Bad Homburg (DE)

(72) Inventors: Philipp Winter, Homberg (DE); Marcus Müller, Ortenberg (DE); Michael Schäfer, Friedberg (DE); Lars Michel, Rosbach v.d. Höhe (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 32 days.

(21) Appl. No.: 17/890,722

(22) Filed: Aug. 18, 2022

(65) Prior Publication Data
US 2023/0055531 A1    Feb. 23, 2023

(30) Foreign Application Priority Data
Aug. 19, 2021   (EP) ..................................... 21192157

(51) Int. Cl.
*A61B 1/00*        (2006.01)
*A61M 25/02*       (2006.01)

(52) U.S. Cl.
CPC ... *A61B 1/00124* (2013.01); *A61M 2025/024* (2013.01)

(58) Field of Classification Search
CPC ........ A61B 1/00124; A61M 2025/024; A61M 2205/16; A61M 5/16881; A61M 39/281
See application file for complete search history.

(56) References Cited

U.S. PATENT DOCUMENTS 5,965,089 A * 10/1999 Jarvik ................. A61M 1/3656
                                                     604/6.11
6,775,117 B2    8/2004 Wodrich et al.
                 (Continued)

FOREIGN PATENT DOCUMENTS

WO      2015046397 A1    4/2015

OTHER PUBLICATIONS

EP Search Report and Written Opinion dated Feb. 15, 2022, issued in connection with counterpart application EP 21 192 157 (EP 4 137 178).

*Primary Examiner* — David M Upchurch
(74) *Attorney, Agent, or Firm* — Cook Alex Ltd.

(57) ABSTRACT

A clamping device for acting onto a medical tubing includes a clamp arrangeable on the medical tubing and displaceable between an open position in which the clamp unblocks the medical tubing and a close position in which the clamp closes the medical tubing. The clamping device further includes a drive system configured to act on the clamp for switching the clamp between the open position and the close position. The clamping device also includes a main control circuit and a secondary control circuit electronically independent from the main control circuit, and a relay switchable between a first position and a second position. In the first position, the relay electronically couples the drive system to the main control circuit while the drive system is electronically decoupled from the secondary control circuit. In the second position, the relay electronically couples the drive system to the secondary control circuit while the drive system is electronically decoupled from the main control circuit. The secondary control circuit causes the clamp to adopt the close position when the relay is in the second position.

12 Claims, 3 Drawing Sheets

(56) References Cited

U.S. PATENT DOCUMENTS

| | | |
|---|---|---|
| 9,707,340 B2 | 7/2017 | Lee et al. |
| 10,195,418 B2 | 2/2019 | Newell et al. |
| 2011/0102052 A1 | 5/2011 | Billingsley et al. |
| 2014/0318639 A1* | 10/2014 | Peret ................... A61M 39/281 251/324 |
| 2017/0312427 A1 | 11/2017 | Steger et al. |
| 2018/0200485 A1* | 7/2018 | Braham ............ A61M 16/0051 |

* cited by examiner

CLAMPING DEVICE FOR ACTING ONTO A MEDICAL TUBING

CROSS-REFERENCE TO RELATED APPLICATION

This application claims the benefit of and priority to European Application No. 21192157.2 filed on Aug. 19, 2021, the disclosure of which is incorporated herein by reference in its entirety.

FIELD

The invention relates to a clamping device for acting onto a medical tubing.

BACKGROUND

The medical tubing may serve to establish a fluidic connection between a medical device and a patient or blood donor. In case of an error, it must be possible to interrupt the fluidic connection and to block any fluid flow through the medical tubing. For this purpose clamping devices are used.

SUMMARY

A clamping device according to the present disclosure comprises a clamp and a drive system. The clamp is arrangeable on the medical tubing and displaceable between an open position in which the clamp unblocks the medical tubing and a close position in which the clamp closes the medical tubing. The drive system is configured to act on the clamp for switching the clamp between the open position and the close position.

The clamp is usually a mechanical clamp. The energy required to bring the clamp into its close position can for example be stored in a tension spring that is continuously tensioned when the clamp is in its open position. As the spring is continuously tensioned there is a risk that the spring breaks suddenly. Furthermore, the assembly of such a clamping device comprising a mechanical clamp and tension spring is quite complex and time consuming. Also, tensioning the spring needs a lot of energy and causes wear-out of the drive system (motor).

It is an object of the instant invention to provide a clamping device which is reliable without the risk of a sudden failure and which can be assembled without major difficulties.

This object is achieved by a clamping device according to the present disclosure.

Accordingly, the clamping device which is provided for acting onto a medical tubing comprises a clamp which is arrangeable on the medical tubing and which is displaceable between an open position in which the clamp unblocks the medical tubing and a close position in which the clamp closes the medical tubing. The clamping device further comprises a drive system that is configured to act on the clamp for switching the clamp between the open position and the close position. The drive system may be or comprise for example an electromotor or an electromagnet.

The clamping device is provided with a main control circuit and a secondary control circuit that is electronically independent from the main control circuit. The main control circuit controls the drive system during normal operation of the clamping device, while the secondary control circuit controls the drive system in case of a fault. A relay electronically connects the drive system with one of the main control circuit and the secondary control circuit. In particular the relay is switchable between a first position and a second position. In the first position the relay electronically couples the drive system to the main control circuit while the drive system is electronically decoupled from the secondary control circuit. In the second position the relay electronically couples the drive system to the secondary control circuit while the drive system is electronically decoupled from the main control circuit. In particular, when the relay is in its first position the drive system can be energized only via the main control circuit and when the relay is in its second position the drive system can be energized only via the secondary control circuit. When the drive system is electronically decoupled from one of the main control circuit and the secondary control circuit, there is no functional connection between the drive system and the respective control circuit by means of the relay or by any other means. When the relay is in its second position, the secondary control circuit causes the clamp to adopt its close position. Conversely, when the relay is in its first position the clamp is controlled by the main control circuit and can adopt its open position, its close position or any position in between the open position and the close position.

The clamping device according to the present disclosure does not require a mechanical clamp and thus avoids the difficulties that come along with the mechanical clamp. Instead the number of specific mechanical components can be reduced. In particular, no mechanical energy storage is needed, such as a continuously tensioned tension spring.

In one embodiment the drive system may be energized by an energy storage or a power supply when the relay is in its second position, that is to say when the drive system is electronically coupled via the relay to the secondary control circuit. In particular, the drive system is energized by an energy storage or a power supply only when the drive system is acting on the clamp for switching the clamp between the open position and the close position and when the relay is in its second position. In contrast, the drive system is not energized by said energy storage/power supply when the relay is in its first position, that is to say when the drive system is electronically coupled via the relay to the main control circuit. When the relay is in its first position, the drive system may be energized by another than said energy storage/power supply. Also with the relay being in its first position, the drive system is energized by the other energy storage/power supply only when the drive system is acting on the clamp for switching the clamp between the open position and the close position. The drive system is not energized as long as it is not acting on the clamp for switching the clamp between the open position and the close position. As most of the time the clamping device is in normal operation mode and the clamp is not switched but intended to be in its open position (the relay being in its first position, electronically coupling the drive system to the main control circuit) for establishing the fluidic connection between the medical device and the patient or blood donor, the power consumption of the clamping device is quite low and in particular reduced with respect to devices such as mechanical clamps that are held in the open position by means of a continuously tensioned spring. Furthermore, as the drive system is energized only when it acts on the clamp for switching the clamp between the open position and the close position, wear of the drive system and noise generation can be reduced. When applying the clamping device to portable, battery driven devices, such as for example a portable blood collection system, the usage time of the battery may be increased or additional functions may be provided.

The secondary control circuit may comprise an energy storage which is configured to energize the drive system for switching the clamp between the open position and the close position when the relay is in its second position and thus electronically couples the drive system to the secondary control circuit. The energy storage may be designed in dependence of the drive system, such that the energy provided by the energy storage for energizing the drive system allows the drive system to close the clamp definitely. In addition, the energy storage may be designed such that the energy provided by the energy storage allows the drive system to keep the clamp closed over a predefined amount of time. For example, the energy storage of the secondary control circuit comprises at least one capacitor. For increasing the energy storage capacity, two or more capacitors may be provided in parallel. Using more than one capacitor has the additional advantage that in case of a fault of one of the capacitors the other capacitor(s) ensure proper supply of electrical energy to the drive system when the relay is in its second position. The at least one capacitor may be a supercapacitor.

In one embodiment the secondary control circuit is configured to switch the relay between the first position and the second position. In particular, the secondary control circuit is configured to switch the relay from the first position into the second position, and vice versa. Switching of the relay may be induced by starting or stopping the supply of electrical energy (provided via the secondary control circuit or the main control circuit) to the relay. For this purpose the secondary control circuit may comprise one or more switches that, depending on their switching state, allow for electrical energy supply to the relay. For example, the one or more switches may be in the form of metal-oxide-semiconductor field-effect transistors (MOSFETs). The electrical energy required for switching the relay may be provided by the energy storage that is provided to energize the drive system or by another power supply. The other power supply may be a power supply (such as a battery) provided for powering the whole clamping device (or even a setup in which the clamping device is integrated). If the secondary control circuit detects or receives a signal as described further below, the relay switches into its second position. As a consequence, the clamp closes powered by the energy storage. For detecting or receiving the signal and switching the relay, a logic-stage is implemented on the secondary control circuit. The logic-stage can comprise transistors, for example metal-oxide-semiconductor field-effect transistors (MOSFETs), or integrated circuits.

The secondary control circuit may be configured to receive and to process a signal representing a fault, such as a system error, power failure or a medical problem. For example the signal may indicate that the voltage of a power supply of the clamping device is below a predefined threshold. Also the signal may be a watchdog signal provided by a watchdog system detecting a failure of the main control circuit of the clamping device. Furthermore, the signal may be provided by a sensor detecting an abnormality in at least one specific condition of the patient or blood donor that is connected via the medical tubing (equipped with the clamping device) to a medical device. For example, the at least one condition of the patient or blood donor may be the blood pressure or heart rhythm/rate of the patient or blood donor. In case that said signal is received by the secondary control circuit, the secondary control circuit causes the relay to switch from the first position into the second position, such that the drive system is electronically connected via the relay to the secondary control circuit. As a result the drive system is energized via the secondary control circuit and the clamp closes. The energy required by the drive system for closing the clamp is provided by the energy storage of the secondary control circuit. In case that said signal is no longer received by the secondary control circuit, the secondary control circuit causes the relay to switch from the second position into the first position, such that the drive system is electronically connected via the relay to the main control circuit. As a result the drive system is energized via the main control circuit and the clamp may open. Here, the required energy may be provided by a power supply of the clamping device.

The main control circuit controls the main functions of the clamping device during normal operation of the clamping device.

In one embodiment the relay is energized when the relay is in its first position. That is to say the relay is energized as long as the drive system is connected to the main control circuit and the clamping device is in normal operation mode. Only with the relay in its first position, the clamp may be in its open position. In this embodiment the reduction of the electrical energy consumption of the clamping device during operation substantially results from the saving of electrical energy for energizing the drive system. In particular, no energy for continuously tensioning a spring is needed.

In one embodiment the relay is not energized when the relay is in its first position. That is to say the relay is not energized as long as the drive system is connected to the main control circuit and the clamping device is in normal operation mode. The relay is only energized when the relay is in or switches into its second position. This is the case if a system error, power failure or a medical problem occurs and a corresponding signal (as described above) is received by the secondary control circuit. In this embodiment the electrical energy consumption of the clamping device during operation is additionally reduced, as most of the time of operation the clamping device is in normal operation mode and the relay is in its first position, electronically coupling the drive system to the main control circuit.

The relay may have different designs. The relay may be provided with two contacts for coupling the drive system to one of the main control circuit and the secondary control circuit. In one embodiment, the relay is a photoMOS-relay.

Also the secondary control circuit may have different designs. Different designs of the secondary control circuit are shown in the Figures.

BRIEF DESCRIPTION OF THE DRAWINGS

The idea underlying the invention shall subsequently be described in more detail with respect to the embodiments shown in the figures. Herein.

DESCRIPTION

Figure 1:
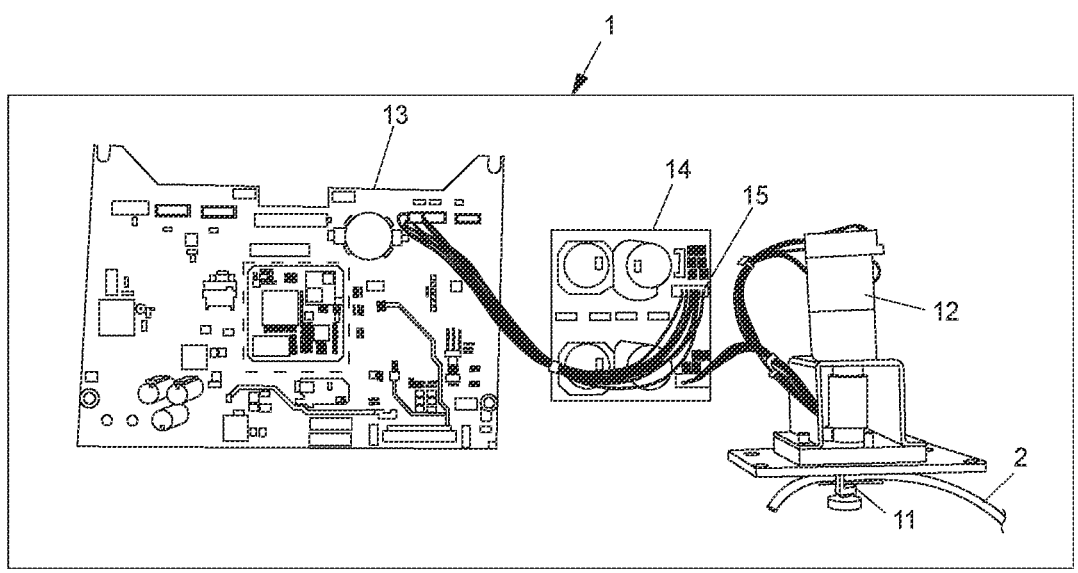
FIG. 1 shows an overview of the main components of a clamping device, namely a clamp, a main control circuit and a secondary control circuit.

FIG. 1 shows components of a clamping device 1 without a housing. The clamping device 1 is shown in combination with a medical tubing 2. The clamping device 1 comprises a clamp 11 and an electromotor 12. In FIG. 1 the clamp 11 is arranged on the medical tubing 2. The clamp 11 is displaceable between an open position in which the clamp 11 unblocks the medical tubing 2 and a close position in which the clamp 11 closes the medical tubing 2. The electromotor 12 forms a drive system for acting on the clamp 11 in order to displace the clamp 11 between its open position and close position. The clamping device 1 is energized by a power supply 15, such as a battery.

The clamping device 1 comprises a main control circuit 13 which controls the main functions of the clamping device 1 during normal operation of the clamping device 1. The main functions of the clamping device 1 comprise opening the clamp, closing the clamp or bringing the clamp into any position by means of the main control circuit (with an encoder). The clamping device 1 further comprises a secondary control circuit 14. The secondary circuit 14 is adapted to receive a signal representing a system error (an error in the main control circuit) and a signal representing a failure of the power supply of the clamping device 1.

By means of a relay 16 the electromotor 12 can be electronically connected either to the main control circuit 13 or to the secondary control circuit 14.

Figure 2:
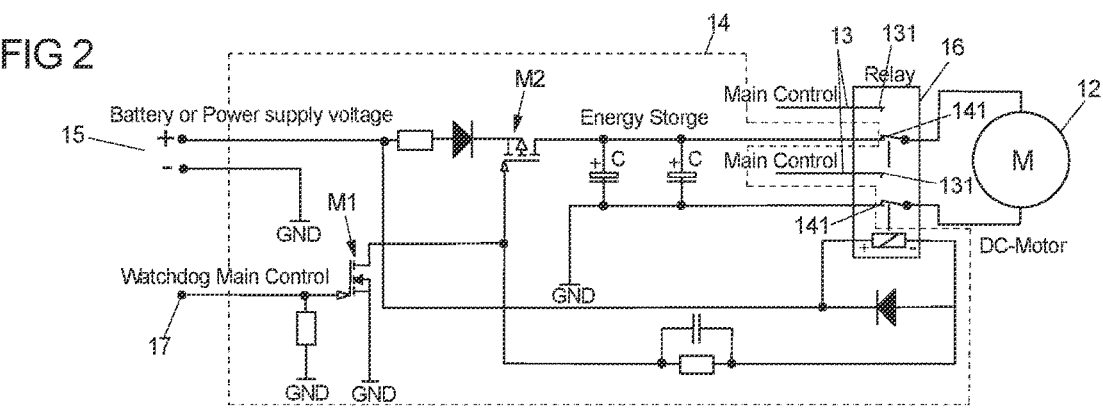
FIG. 2 shows a circuit diagram of the clamping device with a secondary control circuit according to a first embodiment.

In FIG. 2 a circuit diagram of the secondary control circuit 14 according to a first embodiment is shown. On the left of the circuit diagram are shown the power supply 15 of the clamping device 1 and an input 17 for the signal representing an error in the main control circuit 13. The signal is provided by a watchdog system monitoring the main control circuit 13. On the right of the circuit diagram are shown two contacts 131 of the main control circuit 13, two contacts 141 of the secondary control circuit 14 and the relay 16. The relay 16 is electronically connected to the electromotor 12. The relay 16 switches between a first position, in which the relay 16 is electronically connected to the two contacts 131 of the main control circuit 13 and the clamp 11 may be in the open position (not shown in FIG. 2), and a second position, in which the relay 16 is electronically connected to the two contacts 141 of the secondary control circuit 14 and the clamp 11 is in the close position (shown in FIG. 2). The position of the relay 16 depends on the signal provided by the watchdog and on the voltage level of the power supply 15. The secondary control circuit 14 comprises two MOSFETs M1, M2 that are electronically arranged between the input 17 for the signal representing an error in the main control circuit 13 and the power supply 15 on the one hand and the relay 16 on the other hand. Depending on said signal and the voltage level of the power supply 15 the MOSFETs M1, M2 are conductive or non-conductive.

The secondary control circuit 14 comprises two capacitors C connected in parallel that serve as energy storage for the electromotor 12 when the relay 16 electronically connects the electromotor 12 to the secondary control circuit 14. The energy storage C is charged by the power supply 15 only if the voltage level of the power supply 15 is normal and if no error in the main control circuit 13 occurs.

The relay 16 and the secondary control circuit 14 shown in FIG. 2 are designed such that the relay 16 is energized (by the power supply 15 via the secondary control circuit 14) when the relay 16 is in its first position, that is to say when the clamp 11 may be in its open position. This is the case if the voltage level of the power supply 15 is normal and if the input 17 receives no signal representing an error in the main control circuit 13.

In the following will be described different scenarios for illustrating the operation of the clamping device 1 comprising the secondary control circuit 14 shown in FIG. 2.

In a first scenario the voltage level of the power supply 15 is normal (above a predefined threshold) and the signal provided by the watchdog is high indicating that the main control circuit 13 operates properly. In this scenario MOSFET M1 which is an enhancement mode n-channel MOSFET is conductive and MOSFET M2 which is an enhancement mode p-channel MOSFET is conductive. As a consequence, the capacitors C are charged by the power supply 15, the relay 16 is energized by the power supply 15 and the relay 16 is in its first position in which the relay 16 electronically connects the electromotor 12 to the main control circuit 13 (not shown in FIG. 2). The clamp 11 may be in its open position. This scenario corresponds to a normal operation mode of the clamping device 1.

In a second scenario the voltage of the power supply 15 is low (below a predefined threshold) and the signal provided by the watchdog is high indicating that the main control circuit 13 operates properly. In this scenario MOSFET M1 is conductive and MOSFET M2 is non-conductive. As a consequence, the relay 16 is no longer energized by the power supply 15. Therefore, the relay 16 switches into its second position in which the relay 16 electronically connects the electromotor 12 to the secondary control circuit 14 (shown in FIG. 2). Also, the capacitors C are no longer charged by the power supply 15, but provide the stored electrical energy to the electromotor 12. The electromotor 12 acts on the clamp 11 and the clamp 11 switches into its close position.

In a third scenario the voltage of the power supply 15 is normal (above a predefined threshold) and the signal provided by the watchdog is low indicating an error in the main control circuit 13. In this scenario MOSFET M1 is non-conductive and MOSFET M2 is conductive. As a consequence, the secondary control circuit 14 is interrupted so that the relay 16 is no longer energized by the power supply 15. Therefore, the relay 16 switches into its second position in which the relay 16 electronically connects the electromotor 12 to the secondary control circuit 14 (shown in FIG. 2). Also, the capacitors C provide the stored electrical energy to the electromotor 12. The electromotor 12 acts on the clamp 11 and the clamp 11 switches into its close position.

Figure 3:
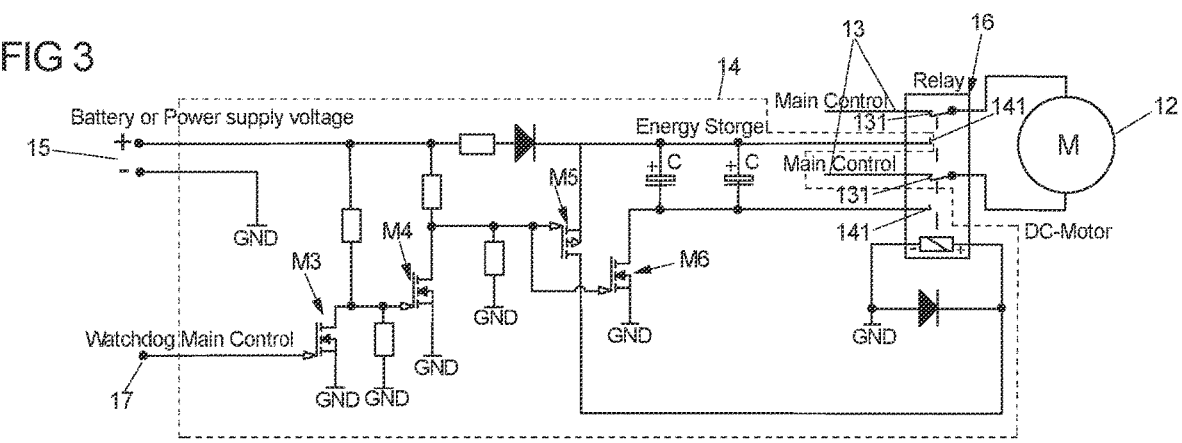
FIG. 3 shows a circuit diagram of the clamping device with a secondary control circuit according to a second embodiment.

In FIG. 3 a circuit diagram of the secondary control circuit 14 according to a second embodiment is shown. This circuit diagram differs from that shown in FIG. 2 in particular in that, instead of two, four MOSFETs M3, M4, M5 and M6 are electronically arranged between the input 17 for the signal representing an error in the main control circuit 13 and the power supply 15 on the one hand and the relay 16 on the other hand. The relay 16 and the secondary control circuit 14 shown in FIG. 3 are designed such that the relay 16 is not energized (via the secondary control circuit 14) when the relay 16 is in its first position, that is to say when the clamp 11 may be in its open position. Instead the relay 16 is energized (by the power supply 15 or by the energy storage C via the secondary control circuit 14) when the relay 16 is in its second position with the clamp 11 being in its close position. This is the case if the voltage level of the power supply 15 is low and/or if the input 17 receives a signal representing an error in the main control circuit 13.

In the following will be described different scenarios for illustrating the operation of the clamping device 1 comprising the secondary control circuit 14 shown in FIG. 3.

In a first scenario the voltage of the power supply 15 is normal (above a predefined threshold) and the signal provided by the watchdog is high indicating that the main control circuit 13 operates properly. In this scenario MOSFET M3 which is an enhancement mode n-channel MOSFET is conductive. MOSFET M4 which is an enhancement mode n-channel MOSFET is non-conductive. MOSFET M5 which is an enhancement mode p-channel MOSFET is non-conductive. MOSFET M6 which is an enhancement mode n-channel MOSFET is conductive. As a consequence, the capacitors C are charged by the power supply 15, the relay 16 is not energized by the power supply 15 and the relay 16 is in its first position in which the relay 16 electronically connects the electromotor 12 to the main control circuit 13 (shown in FIG. 3). The clamp 11 may be in its open position. This scenario corresponds to a normal operation mode of the clamping device 1.

In a second scenario the voltage of the power supply 15 is low (below a predefined threshold) and the signal provided by the watchdog is high indicating that the main control circuit 13 operates properly. In this scenario MOSFETs M3 and M5 are conductive and MOSFETs M4 and M6 are non-conductive. As a consequence, the relay 16 is energized by the capacitors C, because current can flow through the body diode of MOSFET M6 (in reverse mode). Therefore, the relay 16 switches into its second position in which the relay 16 electronically connects the electromotor 12 to the secondary control circuit 14 (not shown in FIG. 3). Also, the capacitors C are no longer charged by the power supply 15, but provide the stored electrical energy to the electromotor 12. (MOSFET M6 limits the energy provided to the electromotor 12 to only the energy available from the energy storage C.) The electromotor 12 acts on the clamp 11 and the clamp 11 switches into its close position.

In a third scenario the voltage of the power supply 15 is normal (above a predefined threshold) and the signal provided by the watchdog is low indicating an error in the main control circuit 13. In this scenario MOSFETs M3 and M6 are non-conductive and MOSFETs M4 and M5 are conductive. As a consequence, the relay 16 is energized by the power supply 15. Therefore, the relay 16 switches into its second position in which the relay 16 electronically connects the electromotor 12 to the secondary control circuit 14 (not shown in FIG. 3). Also, the capacitors C energize the electromotor 12 (the power supply 15 does not energize the electromotor 12 as MOSFET M6 is non-conductive). The electromotor 12 acts on the clamp 11 and the clamp 11 switches into its close position.

Figure 4:
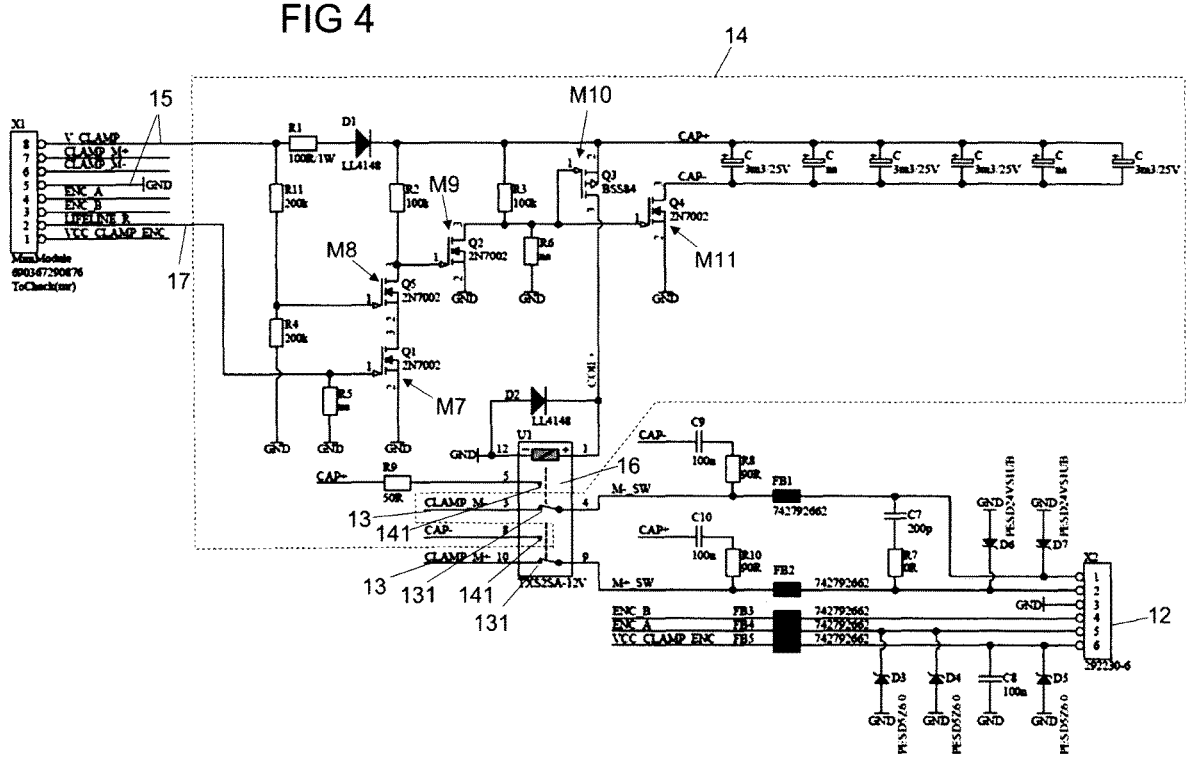
FIG. 4 shows a circuit diagram of the clamping device with a secondary control circuit according to a third embodiment.

In FIG. 4 a circuit diagram of the secondary control circuit 14 according to a third embodiment is shown. This circuit diagram differs from that shown in FIG. 3 in particular in that instead of four, five MOSFETs M7, M8, M9, M10 and M11 are electronically arranged between the input 17 for the signal representing an error in the main control circuit 13 and the power supply 15 on the one hand and the relay 16 on the other hand. Furthermore, instead of two capacitors C, six capacitors C are provided in parallel that serve as energy storage for the electromotor 12 when the relay 16 electronically connects the electromotor 12 to the secondary control circuit 14. The secondary control circuit 14 comprises several resistances, wherein resistance R1 is provided to limit the loading current of the capacitors C and wherein resistance R9 is provided to limit the unload current of the capacitors C towards the electromotor 12. A diode D1 is provided to separate the power supply 15 from the secondary control circuit 14 in case of the second and third scenario described further below.

The relay 16 and the secondary control circuit 14 shown in FIG. 4 are designed such that the relay 16 is not energized (via the secondary control circuit 14) when the relay 16 is in its first position, that is to say when the clamp 11 may be in its open position. Instead the relay 16 is energized (by the power supply 15 or by the energy storage C via the secondary control circuit 14) when the relay 16 is in its second position with the clamp 11 being in its close position. This is the case if the voltage level of the power supply 15 is low and/or if the input 17 receives a signal representing an error in the main control circuit 13.

In the following will be described different scenarios for illustrating the operation of the clamping device 1 comprising the secondary control circuit 14 shown in FIG. 4.

In a first scenario the voltage of the power supply 15 is normal (above a predefined threshold) and the signal provided by the watchdog is high indicating that the main control circuit 13 operates properly. In this scenario MOSFETs M7 and M8 which are both enhancement mode n-channel MOSFETs and which are connected such as to form a logic AND connection are conductive. As a consequence, MOSFET M9 which is an enhancement n-channel MOSFET is non-conductive. This in turn leads to MOSFET M10 which is an enhancement mode p-channel MOSFET being non-conductive. MOSFET M11 which is an enhancement mode n-channel MOSFET is conductive. Due to conductive MOSFET M11 the capacitors C are charged by the power supply 15. Due to non-conductive MOSFET M10 the relay 16 is not energized by the power supply 15 and the relay 16 is in its first position in which the relay 16 electronically connects the electromotor 12 to the main control circuit 13 (shown in FIG. 4). The clamp 11 may be in its open position. This scenario corresponds to a normal operation mode of the clamping device 1.

In a second scenario the voltage of the power supply 15 is low (below a predefined threshold) and the signal provided by the watchdog is high indicating that the main control circuit 13 operates properly. In this scenario MOSFETs M7, M9 and M10 are conductive and MOSFETs M8 and M11 are non-conductive. As a consequence, the relay 16 is energized by the capacitors C, because current can flow through the body diode of MOSFET M11 (in reverse mode) and MOSFET M10 is conductive. Therefore, the relay 16 switches into its second position in which the relay 16 electronically connects the electromotor 12 to the secondary control circuit 14 (not shown in FIG. 4). Also, the capacitors C are no longer charged by the power supply 15, but provide the stored electrical energy to the electromotor 12. MOSFET M11 limits the energy provided to the electromotor 12 to only the energy available from the energy storage C. The electromotor 12 acts on the clamp 11 and the clamp 11 switches into its close position.

In a third scenario the voltage of the power supply 15 is normal (above a predefined threshold) and the signal provided by the watchdog is low indicating an error in the main control circuit 13. In this scenario MOSFETs M7 and M11 are non-conductive and MOSFETs M9 (M8) and M10 are conductive. As MOSFET M10 is conductive, the relay 16 is energized by the power supply 15. Therefore, the relay 16 switches into its second position in which the relay 16 electronically connects the electromotor 12 to the secondary control circuit 14 (not shown in FIG. 4). Also, the capacitors C are no longer charged by the power supply 15, but energize the electromotor 12. (MOSFET M11 limits the energy provided to the electromotor 12 to only the energy available from the energy storage C. For power supply 15, there is no conductive circuit) The electromotor 12 acts on the clamp 11 and the clamp 11 switches into its close position.

LIST OF REFERENCE NUMERALS

1 Clamping device
11 clamp
12 Electromotor
13 Main control circuit
131 Contact of main control circuit
14 Secondary control circuit
141 Contact of secondary control circuit
15 Power supply
16 relay
17 input
2 Medical tubing
C Capacitor
D1 diode
M1-M11 MOSFET
R1, R9 resistance

The invention claimed is:

1. A clamping device for acting onto a medical tubing, comprising:
   a clamp which is arrangeable on the medical tubing and which is displaceable between an open position in which the clamp unblocks the medical tubing and a close position in which the clamp closes the medical tubing,
   a drive system that is configured to act on the clamp for switching the clamp between the open position and the close position,
   a main control circuit and a secondary control circuit that is electronically independent from the main control circuit, wherein the main control circuit controls the drive systemn during normal operation of the clamping device, and
   a relay that is switchable between a first position and a second position and a power supply for energizing the relay,
   wherein in the first position the relay electronically couples the drive system to the main control circuit while the drive system is electronically decoupled from the secondary control circuit,
   wherein in the second position the relay electronically couples the drive system to the secondary control circuit while the drive system is electronically decoupled from the main control circuit,
   wherein the secondary control circuit causes the clamp to adopt the close position when the relay in the second position,
   wherein the secondary control circuit is configured to receive and to process a signal representing an error in the main control circuit and a signal representing a power failure of the power supply, and
   wherein, in case that the signal is received by the secondary control circuit, the secondary control circuit causes the relay to switch from the first position into the second position.

2. The clamping device according to claim 1, wherein the drive system is energized by an energy storage when the drive system acts on the clamp for switching the clamp between the open position and the close position and when the relay is in the second position and wherein the drive system is not energized by the energy storage when the relay is in the first position.

3. The clamping device according to claim 2, wherein the secondary control circuit comprises the energy storage which is configured to energize the drive system for switching the clamp between the open position and the close position when the relay is in the second position and electronically couples the drive system to the secondary control circuit.

4. The clamping device according to claim 3, wherein the energy storage of the secondary control circuit comprises at least one capacitor.

5. The clamping device according to claim 4, wherein the capacitor is a supercapacitor.

6. The clamping device according to claim 1, wherein the secondary control circuit is configured to switch the relay between the first position and the second position.

7. The clamping device according to claim 1, wherein the relay is not energized when the relay is in the first position.

8. The clamping device according to claim 1, wherein the relay is energized when the relay is in the first position.

9. The clamping device according to claim 1, wherein the relay is a photoMOS-relay.

10. The clamping device according to claim 1, wherein the secondary control circuit comprises:
    two MOSFETs that are electronically arranged between an input for a signal representing an error in the main control circuit and a power supply and the relay, and
    two capacitors connected in parallel that serve as energy storage for the drive system when the relay electronically connects the drive system to the secondary control circuit.

11. The clamping device of claim 1, wherein the secondary control circuit comprises:
    four MOSFETs that are electronically arranged between an input for a signal representing an error in the main control circuit and a power supply and the relay, and
    two capacitors connected in parallel that serve as energy storage for the drive system when the relay electronically connects the drive system to the secondary control circuit.

12. The clamping device of claim 1, wherein the secondary control circuit comprises:
    five MOSFETs that are electronically arranged between an input for a signal representing an error in the main control circuit and a power supply and the relay, and
    six capacitors provided in parallel that serve as energy storage for the drive system when the relay electronically connects the drive system to the secondary control circuit.

* * * * *